US009599602B2

(12) United States Patent
Kevil et al.

(10) Patent No.: US 9,599,602 B2
(45) Date of Patent: Mar. 21, 2017

(54) PLASMA H₂S LEVELS AS BIOMARKERS FOR VASCULAR DISEASE

(71) Applicants: Christopher G. Kevil, Shreveport, LA (US); Elvis A. Peter, Kronenwetter, WI (US); Xinggui Shen, Shreveport, LA (US)

(72) Inventors: Christopher G. Kevil, Shreveport, LA (US); Elvis A. Peter, Kronenwetter, WI (US); Xinggui Shen, Shreveport, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 14/435,231

(22) PCT Filed: Oct. 22, 2013

(86) PCT No.: PCT/US2013/066012
§ 371 (c)(1),
(2) Date: Apr. 13, 2015

(87) PCT Pub. No.: WO2014/066285
PCT Pub. Date: May 1, 2014

(65) Prior Publication Data
US 2015/0233896 A1 Aug. 20, 2015

Related U.S. Application Data

(60) Provisional application No. 61/717,758, filed on Oct. 24, 2012.

(51) Int. Cl.
*A01N 43/42* (2006.01)
*A61K 31/445* (2006.01)
*G01N 33/49* (2006.01)

(52) U.S. Cl.
CPC ..... *G01N 33/4925* (2013.01); *G01N 2800/32* (2013.01); *G01N 2800/324* (2013.01)

(58) Field of Classification Search
None
See application file for complete search history.

(56) References Cited

U.S. PATENT DOCUMENTS 7,708,989 B2   5/2010 Loscalzo et al. ............ 424/94.1
2007/0072798 A1   3/2007 Salonen et al. ................ 514/12

OTHER PUBLICATIONS

Bryan N and Grisham M "Methods to detect nitric oxide and its metabolites in biological samples" Free Radical Biology & Medicine 43:645-657, published online Apr. 29, 2007.*
Shen et al. "Measurement of plasma hydrogen sulfide in vivo and in vitro" Free Radical Biology & Medicine 50:1021-1031, published online Jan. 27, 2011.*
Williams et al. "Nitric Oxide Manipulation: A Therapeutic Target for Peripheral Arterial Disease?" Cardiology Research and Practice vol. 2012, Article ID 656247, published online Mar. 20, 2012.*
Kevil C "Hydrogen Sulfide and Peripheral Aterial Disease" ClinicalTrials.gov Identifier NCT01407172, published Jul. 28, 2011.*
Verhaeghe R "Prophylactic antiplatelet therapy in peripheral arterial disease" Drugs 42 Suppl. 5:51-7, published 1991 (abstract only).*
Creager et al. "A Vascular Disease Thought Leaders Summit Report 2015: Improving Vascular Disease Prevention, Detection and Treatment" American Heart Association Conference Report, published 2015.*
Gey et al. "Management of Peripheral Arterial Disease" American Family Physician 69:525-532, published Feb. 1, 2004.*
Tille J.-C. and Pepper M.S. "Hereditary Vascular Anomalies New Insights Into Their Pathogenesis" Arterioscler. Thromb. Vasc. Biol. 24:1578-1590, published online Jul. 1, 2004.*
Coppola G and Novo S "Statins and Peripheral Aterial Disease: Effects on Claudication, Disease Progression, and Prevention of Cardiovascular Events" Archives of Medical Research 38:479-488. Published 2007.*
Calvert, John W. et al., "Novel Insights Into Hydrogen Sulfide-Mediated Cytoprotection," Antioxidants & Redox Signaling, vol. 12, No. 10, pp. 1203-1217 (2010).
Chen, Li et al., "Imbalance of endogenous homocysteine and hydrogen sulfide metabolic pathway in essential hypertensive children," Chinese Med. J., vol. 120, No. 5, pp. 389-393 (2007).
Coletta, Ciro et al., "Hydrogen sulfide and nitric oxide are mutually dependent in the regulation of angiogenesis and endothelium-dependent vasorelaxation," PNAS, vol. 109, No. 23, pp. 9161-9166 (2012).
Heiss, Christian et al., "Plasma nitroso compounds are decreased in patients with endothelial dysfunction," Journal of the American College of Cardiology, vol. 47, No. 3, pp. 573-579 (2006).
Jain, Sushil K. et al., "In African American type 2 diabetic patients, is vitamin D deficiency associated with lower blood levels of hydrogen sulfide and cyclic adenosine monophosphate, and elevated oxidative stress?" Antioxidants & Redox Signaling, vol. 18, No. 10, pp. 1154-1158 (2013).
Jain, Sushil et al., "Low levels of hydrogen sulfide in the blood of diabetes patients and streptozotocin-treated rats causes vascular inflammation?" Antioxidants & Redox Signaling, vol. 12, No. 11, pp. 1333-1337 (2010).
Jiang, Hai-long et al., "[Changes of the new gaseous transmitter H2S in patients with coronary heart disease]," Di 1 jun yi da xue xue bao=Journal of First Mil. Med. University, vol. 25, No. 8, pp. 951-954 (2005).
Kleinbongard, Petra et al., "Plasma nitrite concentrations reflect the degree of endothelial dysfunction in humans," Free Radical Biology & Medicine, vol. 40, pp. 295-302 (2006).

(Continued)

*Primary Examiner* — Christina Bradley
*Assistant Examiner* — Zachary J Miknis
(74) *Attorney, Agent, or Firm* — Davis & Bujold, PLLC; Michael J. Bujold

(57) ABSTRACT

Hydrogen sulfide ($H_2S$) levels in plasma are useful in diagnosing cardiovascular disease. The ratio of $H_2S$ to NO in plasma is useful in diagnosing peripheral artery disease.

6 Claims, 4 Drawing Sheets

(56) References Cited

OTHER PUBLICATIONS

Kovačić, Dragan et al., "Total Plasma Sulfide in Congestive Heart Failure," J. of Cardian Failure, vol. 18, No. 7, pp. 541-548 (2012).
Li, X.H. et al., "Changes in plasma hydrogen sulfide and nitric oxide levels and their clinical significance in children with Kawasaki disease," Chinese Medical Journal, vol. 124, No. 21, pp. 3445-3449 (2011).
Liu, X.Q. et al., "[Plasma levels of endogenous hydrogen sulfide and homocysteine in patients with Alzheimer's disease and vascular dementia and the significance thereof]," Zhonghua yi xue za zhi, vol. 88, pp. 2246-2249 (2008) Abstract.
Sun, N.L. et al., "[Plasma hydrogen sulfide and homocysteine levels in hypertensive patients with different blood pressure levels and complications]," Zhonghua Xin Xue Guan Bing Za Zhi, vol. 35, No. 12, pp. 1145-1148 (2007) Abstract.
Toohey, J., "Possible Involvement of Sulfane Sulfur in Homocysteine-Induced Atherosclerosis," Med. Hypotheses, vol. 56, No. 2, pp. 259-61 (2001) Abstract.

* cited by examiner

PLASMA H₂S LEVELS AS BIOMARKERS FOR VASCULAR DISEASE

This is the United States national stage of international application PCT/US2013/066012, international filing date Oct. 22, 2013, which claims the benefit of the Oct. 24, 2012 filing date of U.S. provisional patent application Ser. No. 61/717,758 under 35 U.S.C. §119(e). The complete disclosure of the priority application is hereby incorporated by reference in its entirety.

TECHNICAL FIELD

This invention pertains to biomarkers for vascular disease.

BACKGROUND ART

Nitric oxide (NO) and hydrogen sulfide ($H_2S$) are gasotransmitters (gaseous signaling molecules) with many different functions in human biology, including specific roles in cardiovascular physiology. $H_2S$ is a colorless, pungent gas that has multiple functions in physiology, including regulation of neurological function, intestinal inflammation, ischemia reperfusion injury, vasomotor tone regulation, and angiogenesis. NO plays critical roles in regulating vasomotor tone, inflammation, platelet activation, ischemic reperfusion injury, neurological function, and ischemic vascular remodeling. Both of these gaseous mediators are synthesized through enzymatic and non-enzymatic pathways. NO production classically occurs in an enzymatic manner via nitric oxide synthase isoenzymes, with non-enzymatic reduction of nitrite/nitrate serving as an alternative pathway. $H_2S$ is produced by three principal enzymes (cystathionine γ-lyase, cystathionine β-synthase, and 3-mercaptopyruvate transferase), with non-enzymatic generation via glutathione and other sulfane sulfur redox pathways. The biological effects of NO and $H_2S$ occur predominately through small molecule interactions and post-translational protein thiol modifications.

A clear understanding of $H_2S$ bioavailability and metabolism has been impeded by controversies in its measurement. It is now well-established that non-analytical methods have produced anomalous measurements. The most widely used assay, the methylene blue method, lacks specificity and is subject to various sources of error in the measurement of bioavailable free $H_2S$. Aside from problematic assay methods, there remains a paucity of information regarding plasma free $H_2S$ levels in normal human physiology and disease states, and regarding the relationship between hydrogen sulfide and nitric oxide bioavailability. The few papers that have explored this area have been hampered by the use of older assay methods and their associated limitations. Recent advances have produced accurate and reliable analytical approaches for measuring free bioavailable $H_2S$, including the ability to distinguish $H_2S$ bioavailability from different tissues. Information has also been obtained regarding plasma free $H_2S$ levels in young healthy adults; however, there is no comparable information for patients with cardiovascular disease.

It has recently been found that $H_2S$ can be used as an alternative to NO in promoting vasodilation. $H_2S$ also plays a role in regulating atherogenesis at the cellular and molecular levels. In addition, $H_2S$ can affect endothelial nitric oxide synthase (eNOS) expression and function while increasing nitrite anion reduction to NO, thereby providing an alternate pathway to regulate NO bioavailability. However, no information currently exists regarding biochemical relationships between NO and $H_2S$ in clinical settings.

Coronary Artery Disease (CAD) and Peripheral Artery Disease (PAD) currently afflict millions of adults in the U.S. and worldwide. However, early, asymptomatic CAD and PAD individuals often remain undiagnosed. Only about a third of U.S. PAD patients receive recommended therapies for secondary prevention. There exists an unfilled need for easy-to-implement diagnostic tests for PAD and CAD.

Several studies suggest that $H_2S$ plays important roles in atherosclerosis pathogenesis, ischemic vascular remodeling, and tissue ischemia reperfusion injury. $H_2S$ has been shown to decrease oxidation of low-density lipoprotein (LDL) and to decrease the uptake of oxidized LDL by macrophages in antioxidant responses. $H_2S$ impairs the migration of monocytes into the subendothelial layer via reduced expression of intercellular adhesion molecule-1 and monocyte chemoattractant protein-1. $H_2S$ has also been found to inhibit foam cell formation and to inhibit vascular smooth muscle cell proliferation. $H_2S$ has been reported to reduce vascular calcification in a rat model via down regulation of alkaline phosphatase activity and osteopontin gene down regulation.

Kleinbongard P, et al., Plasma nitrite concentrations reflect the degree of endothelial dysfunction in humans. *Free radical biology & medicine*. 2006; 40:295-302 reported that plasma nitrite levels are inversely related to the number of cardiovascular risk factors, such that the greater the number of risk factors, the lower the plasma nitrite levels.

In experimental systems it has been reported that plasma free $H_2S$ and NO have an influence upon one another. C. Coletta et al., Hydrogen sulfide and nitric oxide are mutually dependent in the regulation of angiogenesis and endothelium-dependent vasorelaxation. *Proceedings of the National Academy of Sciences of the United States of America*. 2012; 109:9161-9166.

Differences in total hydrogen sulfide or nitric oxide bioavailability have been reported in studies using various detection methods that cannot detect specific biochemical forms of hydrogen sulfide or nitric oxide metabolites (e.g., the methylene blue method or sulfide-sensitive electrodes). Differences in hydrogen sulfide levels may occur in congestive heart failure, Kawasaki disease, Alzheimer's disease, vascular dementia, hypertension, and coronary heart disease. No prior study has suggested that plasma hydrogen sulfide or nitric oxide metabolites are indicative of peripheral artery disease or coronary artery disease. See, e.g.: Chen L, Ingrid S, Ding Y G, Liu Y, Qi J G, Tang C S, Du J B: Imbalance of endogenous homocysteine and hydrogen sulfide metabolic pathway in essential hypertensive children. Chinese medical journal 2007; 120:389-393; Heiss C, Lauer T, Dejam A, Kleinbongard P, Hamada S, Rassaf T, Matern S, Feelisch M, Kelm M: Plasma nitroso compounds are decreased in patients with endothelial dysfunction. Journal of the American College of Cardiology 2006; 47:573-579; Jain S K, Bull R, Rains J L, Bass P F, Levine S N, Reddy S, McVie R, Bocchini J A: Low levels of hydrogen sulfide in the blood of diabetes patients and streptozotocin-treated rats causes vascular inflammation? Antioxidants & redox signaling 2010; 12:1333-1337; Jain S K, Manna P, Micinski D, Lieblong B J, Kahlon G, Morehead L, Hoeldtke R, Bass P F, 3rd, Levine S N: In African American type 2 diabetic patients, is vitamin D deficiency associated with lower blood levels of hydrogen sulfide and cyclic adenosine monophosphate, and elevated oxidative stress? Antioxidants & redox signaling 2013; 18:1154-1158; Jiang H L, Wu H C, Li Z L, Geng B, Tang C S: [Changes of the new gaseous transmitter H2S in patients with coronary heart disease]. Di 1 jun yi da xue xue bao=Academic journal of the first medical college of PLA 2005; 25:951-954; Kleinbongard P, Dejam A, Lauer T, Jax T, Kerber S, Gharini P, Balzer J, Zotz R B, Scharf R E, Willers R, Schechter A N, Feelisch M, Kelm M: Plasma nitrite concentrations reflect the degree of endothelial dysfunction in humans. Free radical biology & medicine 2006; 40:295-302; Kovacic D, Glavnik N, Marinsek M, Zagozen P, Rovan K, Goslar T, Mars T, Podbregar M: Total plasma sulfide in congestive heart failure. Journal of cardiac failure 2012; 18:541-548; Li X H, Zhang C Y, Wu J X, Zhang T: Changes in plasma hydrogen sulfide and nitric oxide levels and their clinical significance in children with Kawasaki disease. Chinese medical journal 2011; 124:3445-3449; Liu X Q, Liu X Q, Jiang P, Huang H, Yan Y: [Plasma levels of endogenous hydrogen sulfide and homocysteine in patients with Alzheimer's disease and vascular dementia and the significance thereof]. Zhonghua yi xue za zhi 2008; 88:2246-2249; and Sun N L, Xi Y, Yang S N, Ma Z, Tang C S: [Plasma hydrogen sulfide and homocysteine levels in hypertensive patients with different blood pressure levels and complications]. Zhonghua xin xue guan bing za zhi 2007; 35:1145-1148.

Numerous studies have tried to identify useful biomarkers for vascular diseases including PAD. Multiple indicators have been examined, including soluble adhesion molecules, inflammatory mediators, cytokines and other plasma proteins. However, the clinical utility of these markers as an indicator of vascular disease is still not clear and under active investigation. There is an unfilled need for improved biomarkers for cardiovascular disease.

DISCLOSURE OF THE INVENTION

We have discovered that plasma free hydrogen sulfide ($H_2S$) and nitric oxide (NO) levels are biomarkers associated with cardiovascular disease. Measuring the level of plasma free $H_2S$, either alone or in conjunction with measurement of the NO level, provides an indicator of cardiovascular disease due to Coronary Artery Disease (CAD), Peripheral Artery Disease (PAD), or both. Several known markers of vascular inflammation were also measured: plasma thrombospondin-1 (TSP-1), Interleukin-6 (IL-6), and soluble intercellular adhesion molecule-1 (sICAM-1). Multiple regression analyses showed that elevated $H_2S$ levels were associated with cardiovascular disease, independent of diabetes mellitus, hypertension, dyslipidemia, smoking status, race, gender, or age. Patients with PAD alone can be identified by the ratio of plasma $H_2S$ to plasma NO. Patients thus identified as having PAD, CAD, or both, or as being at risk for those diseases may then be given appropriate therapies, including therapies that are otherwise previously known in the art.

To explore the relationship between bioavailable free $H_2S$ and NO in patients with and without vascular disease, we undertook an unbiased observational clinical study to measure these molecules in plasma from patients presenting for coronary or peripheral angiography. We quantified nanomolar amounts of plasma free $H_2S$, using the monobromobimane (MBB) method of $H_2S$ measurement. Plasma total NO levels were measured using tri-iodide chemiluminescent analysis.

We found that the plasma free $H_2S$ levels were significantly elevated in patient populations with any early-stage vascular disease, including PAD and CAD. Increased $H_2S$ levels were an independent risk factor, independent of previously known cardiovascular risk factors, as shown by multiple regression analyses. The plasma levels of $H_2S$ thus are useful as biomarkers for vascular disease, and patients thus identified can be given preventive therapies.

We examined possible alternative interpretations for the observed elevated $H_2S$ levels, e.g., that elevated plasma free $H_2S$ levels might be a compensatory response to endothelial dysfunction and dysregulation of NO bioavailability. Interestingly, we found that plasma NO levels were significantly reduced in all patients with cardiovascular disease as compared to reported normal levels of NO in healthy persons, with subjects having PAD alone showing the greatest deficit in NO levels. We observed that patients with PAD also had higher levels of plasma free $H_2S$ as compared to patients with CAD. These findings suggest that vascular disease mechanisms are different between patients with CAD and patients with PAD.

Plasma free $H_2S$ levels alone did not distinguish the particular form of vascular disease; i.e., whether the patient had CAD, PAD, or both. In addition, plasma TSP-1, IL-6, and sICAM-1 levels did not correlate with $H_2S$ or NO bioavailability in either vascular disease condition. However, we identified a novel inverse relationship with NO bioavailability in patients with PAD. The ratio of plasma free $H_2S$ to NO was significantly greater in patients with PAD alone as compared to patients with CAD alone, or patients with both CAD and PAD, or control patients with no vascular disease. Thus, the ratio of plasma $H_2S$ to plasma NO can be used to identify patients with PAD alone.

The novel method can be used in diagnosing, screening, and determining efficacy of therapeutic treatments for vascular disease. Because it uses standard blood specimens, there is minimal risk of harm to the patient. It is highly sensitive, accurate, and clinically validated.

BRIEF DESCRIPTION OF THE DRAWINGS

FIG. 1A depicts plasma free $H_2S$ in the different types of collection tubes versus lysed red blood cells. FIG. 1B illustrates the amount of cell-free hemoglobin in the collection tubes versus lysed red blood cells.

MODES FOR CARRYING OUT THE INVENTION

Figure 1A:
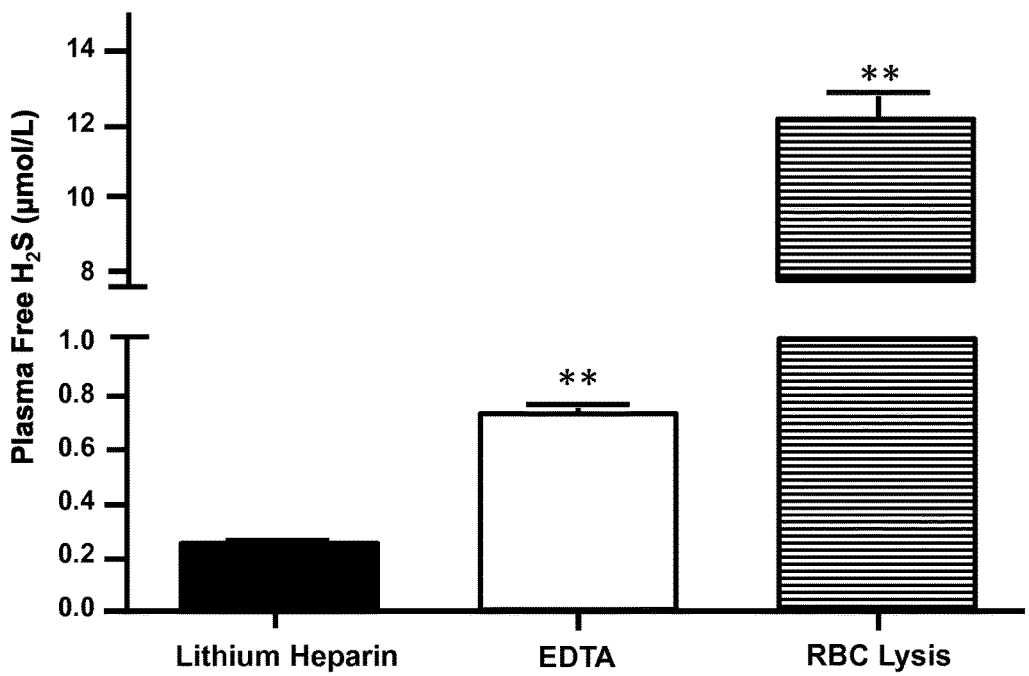
FIGS. 1A and 1B depict the effect of different types of blood collection tubes on plasma $H_2S$ levels.

Embodiments of this invention include a method for diagnosing vascular disease, including early vascular disease (peripheral artery disease, coronary artery disease, or both) in a subject, comprising obtaining a blood sample from the subject, determining the level of free hydrogen sulfide in plasma from the blood sample; and comparing the level of free hydrogen sulfide in the sample to the level of free hydrogen sulfide in a normal control population, wherein a level of hydrogen sulfide in a sample that is significantly greater than the level in the normal control population is indicative of vascular disease.

A second embodiment includes a method for diagnosing peripheral artery disease, including early peripheral artery disease in a subject, comprising obtaining a blood sample from the subject, determining the level of free hydrogen sulfide and the level of nitric oxide in plasma from the blood sample; and comparing the ratio of free hydrogen sulfide to nitric oxide in the sample to the same ratio in a normal control population, wherein a ratio of hydrogen sulfide to nitric oxide in the sample that is significantly above the ratio found in the normal control population is indicative of peripheral artery disease.

METHODS

Abbreviations

| | |
|---|---|
| CAD | Coronary artery disease |
| $H_2S$ | Hydrogen sulfide |
| IL-6 | Interleukin-6 |
| LDL | Low-density lipoprotein |
| NO | Nitric oxide |
| PAD | Peripheral arterial disease |
| sICAM-1 | Soluble Intercellular adhesion molecule-1 |
| TSP-1 | Thrombospondin-1 |

Materials and Tools

| | |
|---|---|
| | 5-sulfosalicylic acid |
| ABI | Ankle brachial index |
| ANCOVA | Analysis of covariance |
| | Drabkin assay |
| DTPA | Diethylenetriaminepentaacetic acid |
| | Eclipse XDB-C18 column |
| EDTA | Ethylenediaminetetraacetic acid |
| ELISA | Enzyme-linked immunosorbent assay |
| | Lithium heparin vacutainer tubes |
| MBB | Monobromobimane |
| Nitric oxide preservation solution | 800 mM potassium ferricyanide, 17.6 mM N-ethylmaleimide, and 6% nonidet P40 |
| RP-HPLC | Reversed phase high-performance liquid chromatography |
| | Shimadzu Prominence HPLC |
| Tris-HCl | Tris-hydrochloride |

Example 1

Study Design

The clinical study complied with the Declaration of Helsinki and was approved by the Institutional Review Board of the Louisiana State University Health Sciences Center at Shreveport (LSUHSC-S). It was registered at www.clinicaltrials.gov, NCT 01407172.

Patients over the age of 40 undergoing cardiac catheterization or peripheral angiogram via a major arterial approach at the LSUHSC-S cardiac catheterization laboratory or vascular surgery suite were enrolled in the study. The protocol broadly enrolled patients with suspected cardiovascular disease, which was then either confirmed or ruled out by angiography. Patients presented for angiography for the usual clinically accepted indications, including coronary angiography, unstable angina, non-ST elevation myocardial infarction, and stable angina. Peripheral angiography was performed for claudication and critical limb ischemia. A single physician operator performed the ankle brachial index (ABI) measurement using the straight wrapping method with an 8 MHz handheld Doppler as recommended by Aboyans V, et al., Measurement and interpretation of the ankle-brachial index: A scientific statement from the American Heart Association. *Circulation*. 2012; 126:2890-2909. ABI was measured prior to angiography in all patients. In this way, patients were recruited and enrolled in an unbiased manner before they were separated into distinct disease cohorts as described in Example 3.

Example 2

Exclusion Criteria

Seventy-eight patients were excluded from the study for various reasons. Patients were excluded if they were unable to provide informed consent, were enrolled in another clinical trial requiring the use of experimental therapeutic agents, were pregnant/nursing, or for other issues (e.g. cancellation of the procedure). Patients with non-atherosclerotic PAD (e.g. Buerger's disease) were excluded, as were those with an ABI>1.3 (indicative of a non-compressible vessel) unless they had already been diagnosed with PAD. To avoid delays in care, patients presenting with ST elevation myocardial infarction or cardiogenic shock were excluded. Samples were also excluded for quality control failures (e.g. exceeding collection tube incubation time or specimen hemolysis).

Example 3

Patient Cohorts and Historical Data

One-hundred ninety-three patients were studied, including 74 PAD patients and 119 non-PAD patients who were subsequently diagnosed with or without CAD after cardiac catheterization. Initial groups were based on the ABI or known PAD status: (1) patients without PAD as defined by 0.9<ABI<1.3; or (2) patients with PAD as defined by an ABI<0.9, or documented PAD on a peripheral angiogram, or with prior peripheral arterial interventions.

The two groups were then divided according to the presence or absence of CAD on the basis of their coronary angiogram using currently accepted definitions, i.e. the presence of stenosis greater than 50% in at least one major epicardial coronary artery (diameter >2 mm). In a few cases, coronary angiography could not be performed, and CAD diagnosis was based on medical history or history of prior myocardial infarction.

Medical records were studied and patient interviews were conducted to assess traditional vascular disease risk factors: hypertension, dyslipidemia, diabetes, obesity, smoking, race, and gender.

Example 4

Blood Collection

Under routine aseptic conditions, a vascular access sheath was placed in the femoral or radial artery. The location was at the operator's discretion. Then 12 ml of blood was collected into a sterile 20 ml syringe after bleed back (to ensure freedom from contamination with the saline used to flush the catheters). The blood sample was directly injected into two plastic 6 ml lithium heparin vacutainer tubes. Lithium heparin collection tubes were preferred, after initial experiments using healthy blood donors had demonstrated decreased hemolysis as compared to EDTA collection tubes, particularly when the EDTA tube was incorrectly filled. After inversion 4-5 times to ensure adequate mixing with anticoagulant, the tube was placed on ice and transported to the research laboratory. To ensure consistency across samples, specimens were centrifuged at 9 minutes after collection, for 4 minutes at 1500×g.

Figure 1B:
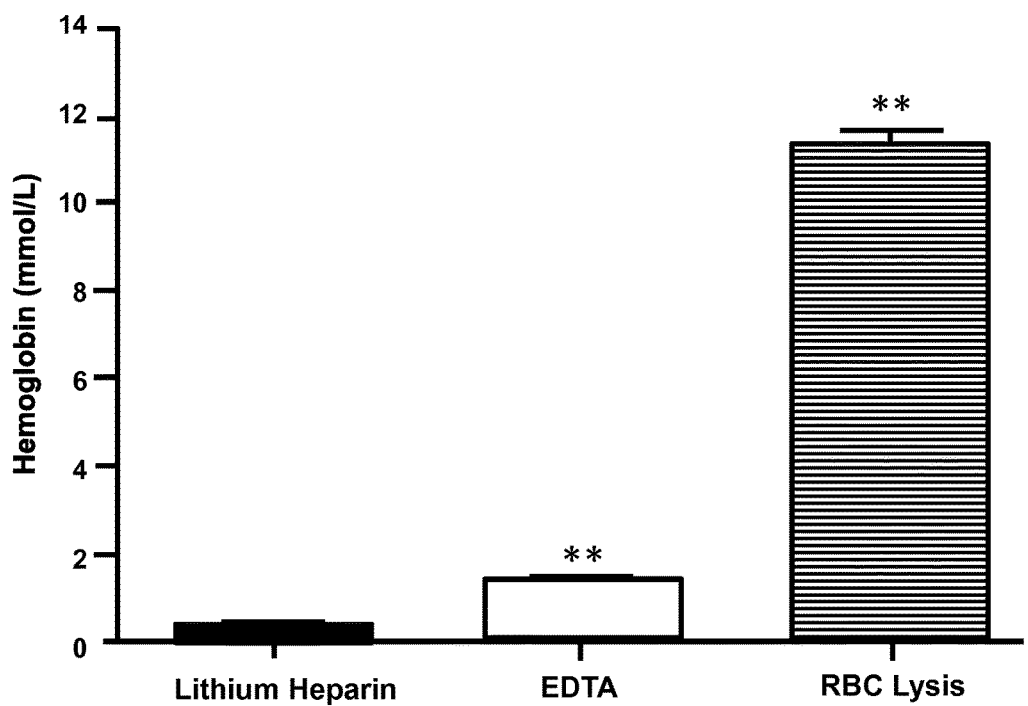

FIGS. 1A and 1B depict the effect of different types of blood collection tubes had on measured plasma $H_2S$ levels. Venous blood was collected from healthy volunteers in either lithium heparin or EDTA vacutainer collection tubes. FIG. 1A depicts plasma free $H_2S$ for the different collection tube types versus lysed red blood cells ($p<0.01$ versus lithium heparin collection tubes). FIG. 1B depicts the amount of cell-free hemoglobin measured using the Drabkin assay in plasma from blood collected in various tube types versus lysed red blood cells ($p<0.01$ versus lithium heparin collection tubes).

Example 5

Measurement of Plasma Free $H_2S$ and Total NO

Plasma samples were analyzed for $H_2S$ as otherwise described in X. Shen et al Measurement of plasma hydrogen sulfide in vivo and in vitro. *Free radical biology & medicine*. 2011; 50:1021-1031. Briefly, plasma free $H_2S$ was measured by reversed-phase high-performance liquid chromatography (RP-HPLC) after derivatization with excess MBB to form the stable sulfide-dibimane derivative. Then 30 μl of plasma was mixed with 70 μl of 100 mM Tris-HCl buffer (pH 9.5, 0.1 mM DTPA), followed by the addition of 50 μl of 10 mM MBB. After 30 minutes, the reaction was stopped by adding 50 μl of 200 mM 5-sulfosalicylic acid. Then the sample was centrifuged and the supernatant was analyzed using a Shimadzu Prominence HPLC with fluorescence detection (λex: 390 nm and λem: 475 nm) and an Eclipse XDB-C18 column. A separate aliquot of plasma was placed in nitric oxide preservation solution (800 mM potassium ferricyanide, 17.6 mM N-ethylmaleimide, and 6% nonidet P40) for tri-iodide NO chemiluminescence analysis. All plasma levels of $H_2S$ or NO were quantified, respectively, with sulfide dibimane and sodium nitrite standard curves. Finally, a third plasma aliquot was used for enzyme-linked immunosorbent assay (ELISA) measurement of TSP-1, IL-6, and sICAM-1 levels using commercially available ELISA assays (R&D Systems, Cayman Chemicals and Thermo scientific respectively) per the manufacturer's instructions.

Example 6

Statistical Analysis

Data were analyzed with Statistical Package for Social Sciences version 16.0 (SPSS for Windows 17 Inc, Chicago, Ill., USA). A p value of $<0.05$ was required for statistical significance. Linear regression analysis, independent samples t-test, Chi-square test, Spearman and Pearson's correlation analysis were performed, based on the normality of the data and type of variable.

RESULTS

Example 7

Demographics and Baseline Characteristics

Clinical characteristics of the enrolled patients were analyzed based on the presence or absence of vascular disease, i.e. patients with either one or both of PAD and CAD, versus those without vascular disease. The data report phenotypic characteristics and associated percentages of the cohorts for characteristics including race, gender, and traditional cardiovascular risk factors (dyslipidemia, diabetes mellitus, hypertension, obesity, smoking). Category percentages per cohort are listed in Table 1. Table 2 lists the frequency with which various pharmaceutical agents (aspirin, Clopidogrel, other antiplatelet, beta blocker, ACE/ARB, statin, Cilostazol) were taken by each patient cohort.

TABLE 1

Patient demographic characteristics

| | | Diagnosis | | | |
|---|---|---|---|---|---|
| | | No vascular disease (N = 53) | Any vascular disease (N = 140) | CAD alone (N = 66) | PAD alone (N = 13) |
| | | Mean ± sd | Mean ± sd | Mean ± sd | Mean ± sd |
| Age | | 53 ± 8.6 | 57 ± 8.5 | 55 ± 8.7 | 58 ± 8.0 |
| | | Count (N %) | Count (N %) | Count (N %) | Count (N %) |
| Gender | Male | 15 (28.3%) | 85 (60.7%) | 39 (59.1%) | 9 (69.2%) |
| | Female | 38 (71.7%) | 55 (39.3%) | 27 (40.9%) | 4 (30.8%) |
| Race | Non-black | 14 (26.4%) | 66 (47.1%) | 38 (57.6%) | 5 (38.5%) |
| | Black | 39 (73.6%) | 74 (52.9%) | 28 (42.4%) | 8 (61.5%) |
| Dyslipidemia | No | 32 (60.4%) | 38 (27.1%) | 19 (28.8%) | 4 (30.8%) |
| | Yes | 21 (39.6%) | 102 (72.9%) | 47 (71.2%) | 9 (69.2%) |
| Diabetes mellitus | No | 36 (67.9%) | 85 (60.7%) | 38 (57.6%) | 9 (69.2%) |
| | Yes | 17 (32.1%) | 55 (39.3%) | 28 (42.4%) | 4 (30.8%) |
| Hypertension | No | 10 (18.9%) | 10 (7.1%) | 3 (4.5%) | 2 (15.4%) |
| | Yes | 43 (81.1%) | 130 (92.9%) | 63 (95.5%) | 11 (84.6%) |
| Obesity | Non-obese | 17 (32.1%) | 68 (48.6%) | 28 (42.4%) | 8 (61.5%) |
| | Obese | 36 (67.9%) | 72 (51.4%) | 38 (57.6%) | 5 (38.5%) |
| Smoking | Non-smoker | 37 (69.8%) | 70 (50%) | 35 (53.0%) | 4 (30.8%) |
| | Smoker | 16 (30.2%) | 70 (50%) | 31 (47.0%) | 9 (69.2%) |

TABLE 2

Patient medications taken

| Home Medications | | No vascular disease Count | No vascular disease N % | Any vascular disease Count | Any vascular disease N % | CAD alone Count | CAD alone N % | PAD alone Count | PAD alone N % |
|---|---|---|---|---|---|---|---|---|---|
| Aspirin | No | 24 | 45.3% | 42 | 30.0% | 18 | 27.3% | 3 | 23.1% |
|  | Yes | 29 | 54.7% | 98 | 70.0% | 48 | 72.7% | 10 | 76.9% |
| Clopidogrel | No | 46 | 86.8% | 92 | 65.7% | 46 | 69.7% | 12 | 92.3% |
|  | Yes | 7 | 13.2% | 48 | 34.3% | 20 | 30.3% | 1 | 7.7% |
| Other antiplatelet | No | 53 | 100.0% | 138 | 98.6% | 65 | 98.5% | 12 | 92.3% |
|  | Yes | 0 | 0.0% | 2 | 1.4% | 1 | 1.5% | 1 | 7.7% |
| Beta blocker | No | 21 | 39.6% | 43 | 30.7% | 18 | 27.3% | 10 | 76.9% |
|  | Yes | 32 | 60.4% | 97 | 69.3% | 48 | 72.7% | 3 | 23.1% |
| ACE/ARB | No | 28 | 52.8% | 38 | 27.1% | 20 | 30.3% | 5 | 38.5% |
|  | Yes | 25 | 47.2% | 102 | 72.9% | 46 | 69.7% | 8 | 61.5% |
| Statin | No | 28 | 52.8% | 40 | 28.6% | 18 | 27.3% | 5 | 38.5% |
|  | Yes | 25 | 47.2% | 100 | 71.4% | 48 | 72.7% | 8 | 61.5% |
| Cilostazol | No | 53 | 100% | 137 | 97.9% | 66 | 100% | 12 | 92.3% |
|  | Yes | 0 | 0.0% | 3 | 2.1% | 0 | 0.0% | 1 | 7.7% |

Example 8

Plasma Free $H_2S$ and Vascular Disease

Linear regression analysis and independent samples t-test were employed to examine the relationship between $H_2S$ bioavailability and specific cardiovascular disease status. Plasma free $H_2S$ levels in patients with either vascular disease (mean=441.0 nM) were significantly elevated compared to patients without vascular disease (mean=368.5 nM, p=0.01). Importantly, the elevated $H_2S$ levels that were seen in patients with either vascular disease, as compared to those without vascular disease, were independent of traditional risk factors including age, race, gender, and history of diabetes mellitus, hypertension, hyperlipidemia, smoking, or obesity. Likewise, plasma free $H_2S$ levels in patients with PAD alone (mean=514.4 nM, p=0.007) or CAD alone (mean=443.8 nM, p=0.02) were significantly greater than patients without either vascular disease (mean=368.5 nM). However, differences in plasma free $H_2S$ levels between patients with CAD alone versus PAD alone were not statistically significant (p=0.18). Thus, plasma free $H_2S$ alone was not able to discriminate between the two forms of vascular disease at a statistically significant level. Importantly, total NO levels were significantly reduced in patients with PAD alone as compared to patients without vascular disease. Table 3 shows these results.

Example 9

Free $H_2S$ and Smoking Status

An independent samples t-test showed that patients who were current smokers had significantly elevated plasma free $H_2S$ levels (mean=452.28 nM, p=0.03) as compared to those who were not current smokers (mean=396.10 nM). However, linear regression analysis revealed that when controlled for the presence of vascular disease the difference between smokers and non-smokers was not statistically significant (p=0.073). A one-way analysis of covariance (ANCOVA) between subjects was performed to examine the effect of smoking on the relationship between $H_2S$ and vascular disease. ANCOVA revealed that patients with vascular disease had significantly higher adjusted $H_2S$ levels (mean±se=438.54±14.73) as compared to patients without vascular disease (mean±se=375.15±24.11, $F(1,190)$=4.97, p=0.027).

Example 10

Inflammatory Indicators and $H_2S$ Levels

Several inflammatory markers associated with cardiovascular disease were examined, including sICAM-1, IL-6, and TSP-1. There was no significant difference noted among the various inflammatory markers between the patient cohorts, although an increasing trend for IL-6 was noted in patients with PAD alone. (See Table 4.)

TABLE 3

Plasma Free $H_2S$ and Total NO levels in vascular disease.

|  | No vascular disease n = 53 | Any vascular disease n = 140 | CAD alone n = 66 | PAD alone n = 13 |
|---|---|---|---|---|
| Plasma free $H_2S$ (nM) | 368.53 ± 20.87 | 441.04 ± 15.40 (p = 0.010) | 443.89 ± 21.67 (p = 0.020) | 514.48 ± 62.05 (p = 0.007) |
| Total NO levels (nM) | 64.71 ± 1.12 | 64.71 ± 1.07 (p = 0.997) | 61.56 ± 1.09 (p = 0.743) | 38.86 ± 1.20 (p = 0.034) |

All data are reported as mean ± standard error of the mean. P values are compared to the no vascular disease group.

In contrast to the previous study by Smadja et al., we did not observe an increase in plasma TSP-1 levels. This is likely because our study included Caucasian and African-American males and females, whereas, the Smadja et al. study enrolled only "white men younger than 70 years of age." We found that African-American men had significantly lower plasma free $H_2S$ than Caucasian men.

Finally, Pearson correlation analysis did not reveal any significant association between plasma free $H_2S$ and levels of IL-6, sICAM-1, or TSP-1.

TABLE 4

Plasma sICAM-1, IL-6, and TSP-1 levels in vascular disease.

| | No vascular disease n = 53 | Any vascular disease n = 140 | CAD alone n = 66 | PAD alone n = 13 |
|---|---|---|---|---|
| sICAM-1 ng/mg | 365.04 ± 1.05 | 389.16 ± 1.03 (p = 0.324) | 375.40 ± 1.04 (p = 0.704) | 378.80 ± 1.16 (p = 0.766) |
| IL-6 ng/mg | 12.83 ± 1.20 | 17.53 ± 1.12 (p = 0.156) | 13.24 ± 1.17 (p = 0.900) | 25.89 ± 1.37 (p = 0.093) |
| TSP-1 ng/mg | 40.95 ± 2.25 | 37.09 ± 1.37 (p = 0.143) | 37.33 ± 1.95 (p = 0.230) | 32.43 ± 4.05 (p = 0.093) |

All data are reported as mean ± standard error of the mean. P values are compared to no vascular disease group.

Example 11

NO and Vascular Disease

The Kleinbongard et al study reported lower plasma nitrite levels in the presence of a higher number of vascular disease risk factors. Interestingly, we found that patients with no vascular disease had considerably lower plasma total NO levels (mean=64.7 nM) as compared to previously reported 'normal' NO levels of healthy adults (~150-300 nM). However, the patients without clinically-diagnosed vascular disease still had numerous risk factors (Table 1) that are known to contribute to endothelial cell dysfunction and reduced NO levels; thus these results are not inconsistent. Linear regression analysis revealed that plasma total NO levels were only significantly lower only in patients with PAD alone (mean=38.86 nM, p=0.034) as compared to subjects without vascular disease. Together, these data highlight that plasma NO bioavailability was considerably diminished in our study subjects as compared to normal healthy subjects, and that patients with PAD alone had a significant deficit in total NO bioavailability.

Example 12

Ratio of $H_2S$ to NO and Vascular Disease

We examined the relationship between plasma free $H_2S$ and NO. We analyzed the data to discriminate between different forms of vascular disease, but Spearman correlation analysis between plasma NO and free $H_2S$ in all patients with vascular disease did not reveal a significant correlation. We next calculated plasma $H_2S$/NO concentration ratios for each cohort and analyzed the ratio using linear regression analysis. Importantly, the plasma $H_2S$/NO ratio was significantly elevated in the PAD-only group (p=0.031), both as compared to patients with CAD alone, and as compared to those without vascular disease.

Figure 2:
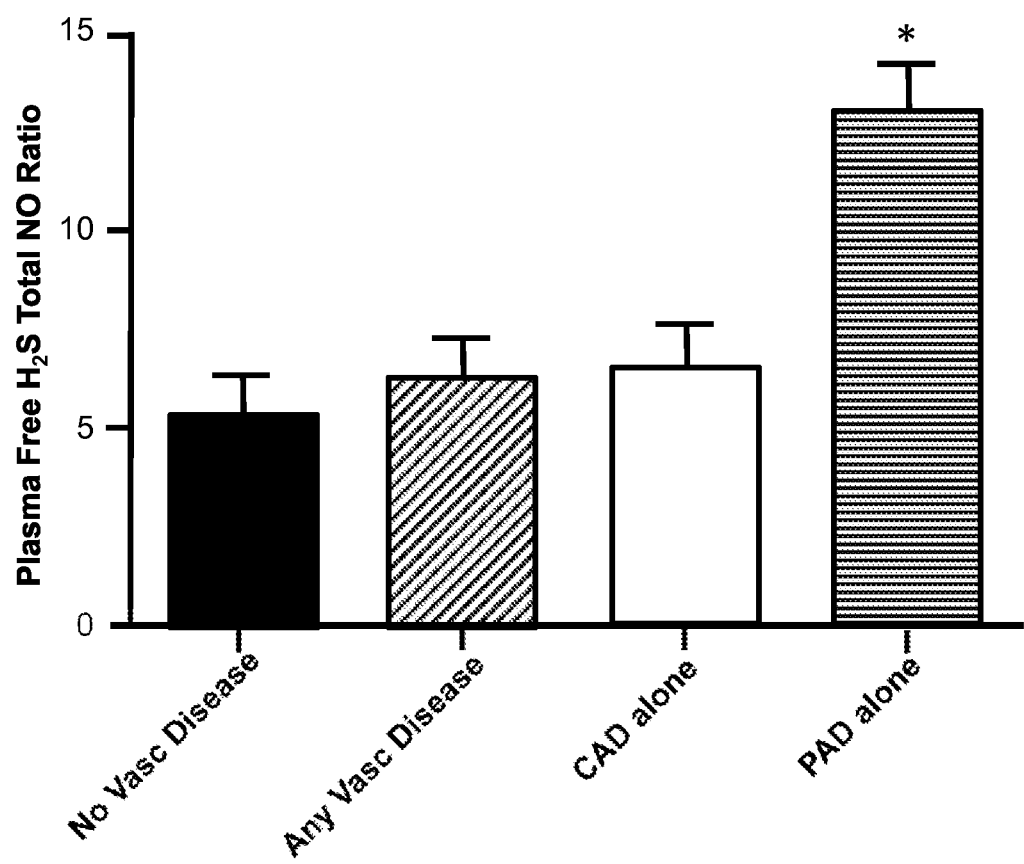
FIG. 2 depicts the ratio of plasma free $H_2S$ to total NO, calculated for different vascular disease cohorts.

FIG. 2 depicts the molar ratio of plasma free $H_2S$ to total NO, for each of the vascular disease cohorts. The free $H_2S$/NO ratio was significantly elevated in patients with PAD alone over all other comparison cohorts, *p<0.05. No vascular disease, n=53; CAD alone, n=66; PAD alone, n=13; and any vascular disease, n=140. Together, these data revealed the novel finding that patients with PAD alone have significantly greater amounts of plasma free $H_2S$ as compared to NO. The data are shown in Table 5. An $[H_2S]$:$[NO]$ molar ratio above about 6.5 is suggestive of PAD. The higher the ratio (greater than 8, greater than 10), the more likely the patient has PAD alone.

TABLE 5

Ratio of plasma $H_2S$ to plasma NO in patient groups.

| Group | No. | Plasma $[H_2S]$:$[NO]$ molar ratio | P value (compared to control) |
|---|---|---|---|
| Control (no CAD or PAD) | 53 | 5.26 ± 1.14 | |
| All PAD | 74 | 5.87 ± 1.13 | 0.513 |
| PAD alone | 13 | 12.06 ± 1.23 | 0.004** |
| PAD or CAD or both | 140 | 6.23 ± 1.08 | 0.260 |
| PAD and CAD | 61 | 5.05 ± 1.14 | 0.830 |
| CAD alone | 66 | 6.62 ± 1.10 | 0.174 |

**PAD alone compared to CAD alone: P-value = 0.031.
**PAD alone compared to PAD and CAD: P-value = 0.002

Possible therapies that could be employed following a diagnosis of decreased plasma $H_2S$ levels include treatment with one or more of the following: statin(s), cilostazol, a suitable NO-based drug or NO prodrug, cardiac catheterization, vascular stent placement, vascular angioplasty, vascular bypass surgery, supervised exercise therapy, or other treatments known in the art for PAD or CAD.

Example 13

Figure 3A:
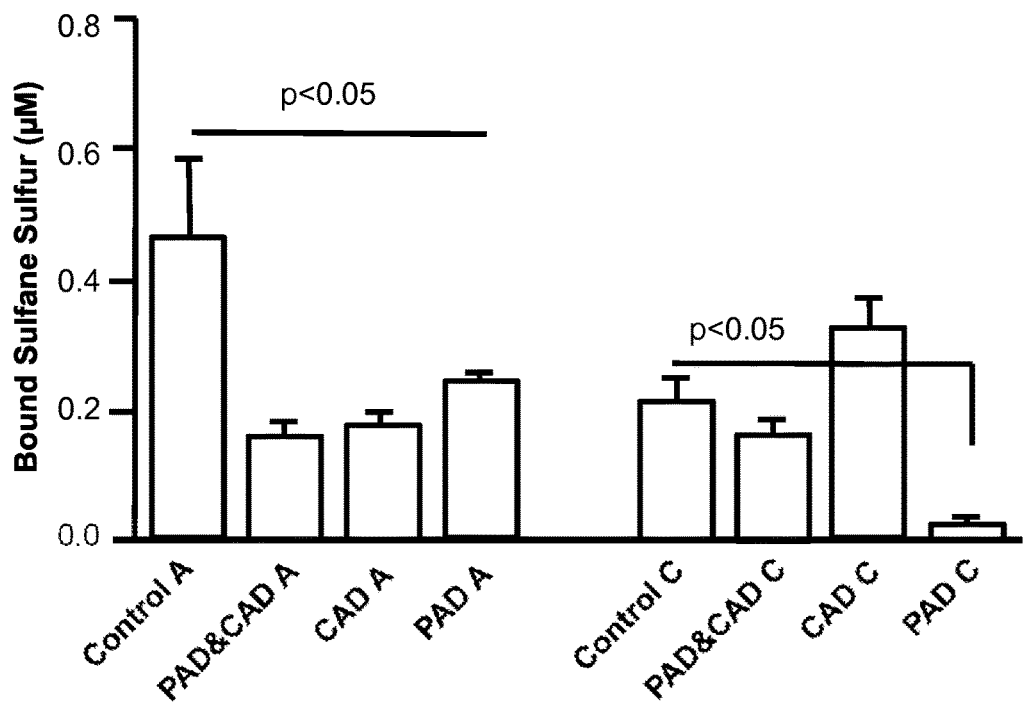
FIGS. 3A-3C illustrate measured levels of plasma total sulfide and bound sulfane sulfur from American males of either African (A) or European (C) ancestry, grouped as having coronary artery disease (CAD), peripheral artery disease (PAD), any form of vascular disease (AVD), or controls without vascular disease. CAD was diagnosed by angiography, PAD was diagnosed by ankle-brachial index measurements.
Figure 3B:
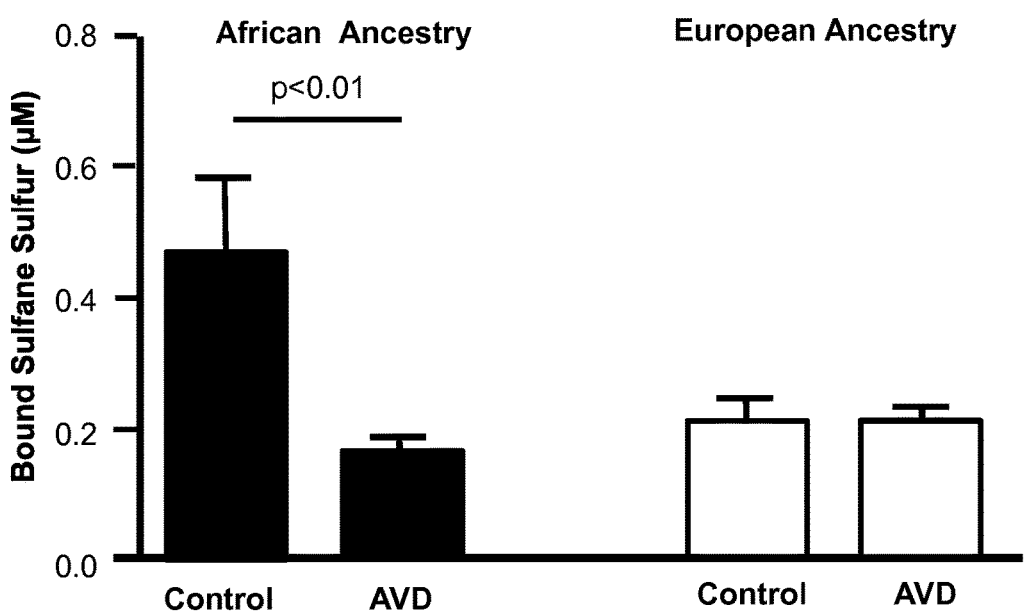
Figure 3C:
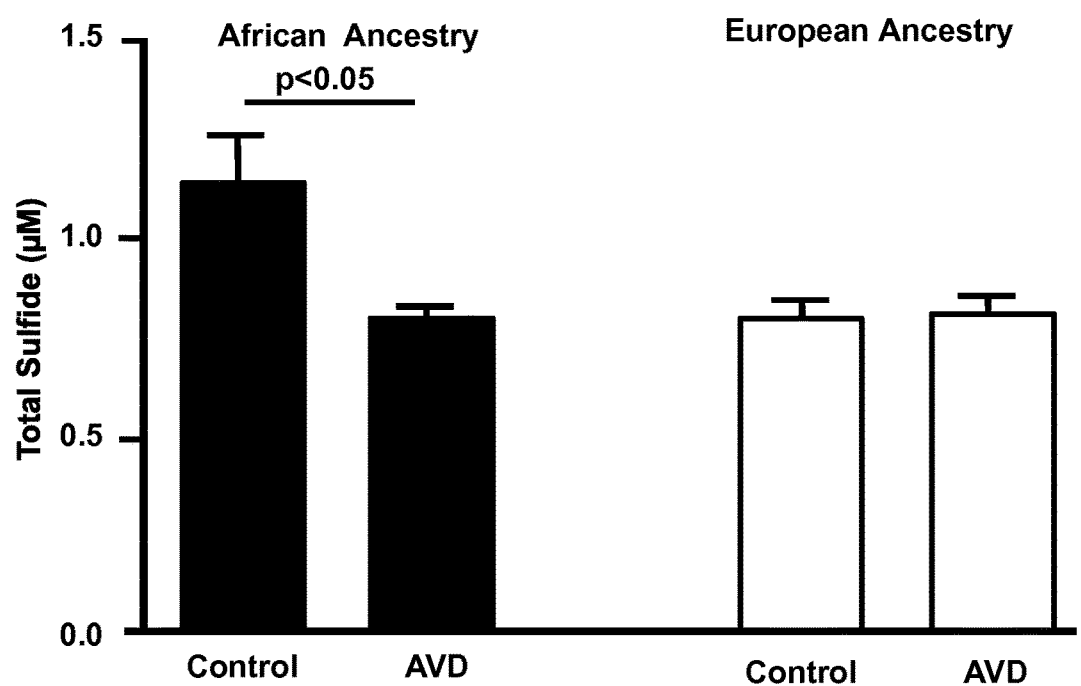

Plasma Total Sulfide and Bound Sulfane Sulfur Indicate Cardiovascular Disease Status Based on Race The relationship between plasma sulfide bioavailability and cardiovascular disease may depend on an individual's race or sex. FIGS. 3A-3C illustrate measured levels of plasma total sulfide and bound sulfane sulfur from American males of either African (A) or European (C) ancestry, grouped as having coronary artery disease (CAD), peripheral artery disease (PAD), any form of vascular disease (AVD), or controls without vascular disease. CAD was diagnosed by angiography. PAD was diagnosed by ankle-brachial index measurements. FIG. 3A depicts that plasma bound sulfane sulfur was significantly reduced in individuals of African ancestry with CAD alone, PAD alone, or both CAD and PAD, as compared to individuals of African ancestry without cardiovascular disease (control). By contrast, in individuals of European ancestry plasma bound sulfane sulfur levels were significantly reduced only for individuals with PAD alone. FIG. 3B depicts that bound sulfane sulfur was significantly reduced in individuals of African ancestry with AVD. FIG. 3C illustrates that, for individuals of African ancestry but not for individuals of European ancestry, plasma total sulfide levels were significantly reduced for individuals with AVD as compared to control. Together, these data demonstrated that decreased plasma bound sulfane sulfur and decreased total sulfide levels are significantly associated with the presence of cardiovascular disease in males of African ancestry. Comparable studies for females will be conducted in the future.

The complete disclosures of all references cited in the specification are hereby incorporated by reference in their entirety, as is the complete disclosure of priority application Ser. No. 61/717,758. In the event of an otherwise irresolvable conflict, however, the disclosure of the present specification shall control.

What is claimed:

1. A method for treating peripheral artery disease in a vertebrate patient, said method comprising the steps of:
   (a) assaying plasma free $H_2S$ concentration and plasma NO concentration in a blood sample from a patient, wherein the plasma free $H_2S$ concentration is assessed using monobromobimane; and identifying the patient as having peripheral artery disease if the ratio of the concentration of plasma free $H_2S$ in the patient to the concentration of plasma NO in the patient is at least 129% higher than a mean ratio in a control population having no peripheral artery disease; and
   (b) administering a therapeutic for peripheral artery disease to the patient if the patient is thus identified as having peripheral artery disease.

2. The method of claim 1 wherein the therapeutic for peripheral artery disease is one of a statin, cilostazol, a suitable NO-based drug or NO prodrug, cardiac catheterization, vascular stent placement, vascular angioplasty, vascular bypass surgery, and supervised exercise therapy.

3. The method of claim 1,
   further comprising the steps of forming a sulfide-dibimane derivative and measuring an amount of sulfide-dibimane to determine the free $H_2S$ concentration in the plasma.

4. A method for treating peripheral artery disease in a vertebrate patient, said method comprising the steps of:
   (a) assaying plasma free $H_2S$ concentration and plasma NO concentration in a blood sample from the patient, wherein the plasma free $H_2S$ concentration is assessed using monobromobimane; and identifying the patient as having peripheral artery disease if the ratio of a molar ratio of the concentration of plasma free $H_2S$ in the patient to the concentration of plasma NO in the patient is above 6.5; and
   (b) administering a therapeutic for peripheral artery disease to the patient if the patient is thus identified as having peripheral artery disease.

5. The method of claim 4, wherein the ratio of the molar ratio of the concentration of plasma free $H_2S$ in the patient to the concentration of plasma NO in the patient is above 8.

6. The method of claim 4, wherein the ratio of the molar ratio of the concentration of plasma free $H_2S$ in the patient to the concentration of plasma NO in the patient is above 10.

* * * * *